United States Patent [19]

Yamashina et al.

[11] Patent Number: 5,211,883
[45] Date of Patent: May 18, 1993

[54] SHAMPOO COMPOSITION

[75] Inventors: Sahoko Yamashina, Tochigi; Seiichi Kumagai, Funabashi; Kazuyuki Yahagi, Tokyo, all of Japan

[73] Assignee: Kao Corporation, Tokyo, Japan

[21] Appl. No.: 767,467

[22] Filed: Sep. 30, 1991

Related U.S. Application Data

[62] Division of Ser. No. 507,752, Apr. 12, 1990, Pat. No. 5,077,041.

[30] Foreign Application Priority Data

Apr. 14, 1989 [JP] Japan ................................. 1-94495

[51] Int. Cl.$^5$ .......................... C11D 1/90; C11D 1/88; C11D 1/66; C11D 9/36
[52] U.S. Cl. .................... 252/546; 252/174.15; 252/174.23; 252/DIG. 2; 252/DIG. 13; 424/70
[58] Field of Search ............. 424/70; 252/546, 174.15, 252/174.23, DIG. 2, DIG. 13

[56] References Cited

U.S. PATENT DOCUMENTS

| | | | |
|---|---|---|---|
| 3,964,500 | 6/1976 | Drakoff | 252/DIG. 13 |
| 4,559,227 | 12/1985 | Chandra et al. | 424/70 |
| 4,597,962 | 7/1986 | Grollier et al. | 424/70 |
| 4,704,272 | 11/1987 | Oh et al. | 252/DIG. 13 |
| 4,741,855 | 5/1988 | Grote et al. | 252/DIG. 13 |
| 4,876,034 | 10/1989 | Hirota et al. | 252/DIG. 13 |
| 4,927,563 | 5/1990 | McCall | 252/DIG. 13 |
| 4,931,216 | 6/1990 | Igarashi et al. | 252/DIG. 13 |
| 4,954,335 | 9/1990 | Janchiprapmuej | 424/70 |

FOREIGN PATENT DOCUMENTS

| | | |
|---|---|---|
| 0078597 | 5/1983 | European Pat. Off. . |
| 0269939 | 6/1988 | European Pat. Off. . |
| 2752116 | 6/1978 | Fed. Rep. of Germany . |
| 63-307810 | 12/1988 | Japan . |
| 2058103 | 4/1981 | United Kingdom . |
| 2165550 | 4/1986 | United Kingdom . |

*Primary Examiner*—W. J. Shine
*Assistant Examiner*—Douglas J. McGinty
*Attorney, Agent, or Firm*—Oblon, Spivak, McClelland, Maier & Neustadt

[57] ABSTRACT

A shampoo composition is disclosed. The composition comprises an amidoamine-type amphoteric surface active agent, a specific type of modified silicone polymeric compound, and a specific type of polymer. It gives an excellent soft and smooth feeling during washing and rinsing, a superb natural hair-set effect without oily stickiness and roughness, and easy passage of comb through the hair. It is also mild to the skin, the mucous of the eyes, and the like.

12 Claims, No Drawings

SHAMPOO COMPOSITION

This is a division of application Ser. No. 07/507,752, filed on Apr. 12, 1990, now U.S. Pat. No. 5,077,041.

BACKGROUND OF THE INVENTION

1. Field of the Invention

This invention relates to a shampoo composition, and, more particularly, to a shampoo composition comprising an amidoamine-type amphoteric surface active agent, a specific type of modified silicone polymeric compound, and a specific type of polymer. The shampoo composition gives an excellent soft and smooth feeling during washing and rinsing, a superb natural hair-set effect without oily stickiness and roughness, and easy passage of comb through the hair. It is mild to the skin and the mucous of the eyes and the like.

2. Description of the Background Art

Conventionally, anionic surfactants such as alkyl sulfates, polyoxyethylenealkyl sulfates, alkylbenzene sulfonates, o-olefin sulfonates, and the like have widely been used as surfactants for shampoos. These surfactants, however, are more or less irritative to the skin, and roughen the skin if continuously used. On the other hand, amidoamine-type amphoteric surface active agents are known to be very mild surfactants which give only a little irritation to the skin. More recently, amidoamine-type amphoteric surface active agents having a wider applicability such as those disclosed in Japanese Patent Application Laid-open No. 128100/1988 are used as the base components of shampoos instead of anionic surfactants.

If, however, an addition of a conventional cationic polymer to a shampoo containing an amidoamine-type amphoteric surface active agent as a base component in order to promote its conditioning effect causes unfavorable stickiness when the hair is being dried resulting in starchy, stiff hair due to solid complexes produced by the cationic polymer and the surface active agent. Thus, an addition of a cationic polymer does not give a favorable feeling to the hair after drying, although it can promote light wet feeling and softness. Japanese Patent Application Laid-open Nos. 45406/1981, 74602/1984, 36407/1985, and 56916/1985 disclose shampoo compositions having improved conditioning effects by the addition of silicon-containing cationic polymers, amino-modified organopolysiloxane emulsions, or the like. None of them, however, discloses a shampoo composition imparting low irritation, exhibiting a good conditioning effect, and giving a favorable, natural, dry hair-set. Japanese Patent Application Laid-open No. 307810/1988 discloses a shampoo composition containing an amphoteric surface active agent and an amino-modified organopolysiloxane emulsion. The advantage of the compound, however, is limited to the conditioning effect after hair washing. Good feeling effects during washing and rinsing cannot be obtained by the simple use of an amino-modified organopolysiloxane emulsion. Japanese Patent Application Laid-open No. 36407 discloses a combined use of a cationic polymer having an amino group or an ammonium group in the main chain and a silicon-containing cationic polymer. The presence of an amino group or an ammonium group in the main chain of a cationic polymer decreases mutual solubility between the cationic polymer and surface active agents. This produces stiffened hair resulting in poor conditioning effects.

Therefore, development of a shampoo composition which possesses an advantageous feature of amidoamine-type amphoteric surface active agents, while giving an excellent feeling upon use all through washing, rinsing, and drying has been desired.

Quality of foam and viscosity are crucial for a shampoo to be a decent commercial product. Shampoos which are superb from the aspect not only of conditioning effects but also of foam quality and usability have been desired.

In view of this situation, the present inventors have undertaken extensive studies and have found that a shampoo composition comprising an amidoamine-type amphoteric surface active agent, a specific type of modified silicone polymeric compound, and a specific type of polymer exhibited improved conditioning effects was mild to the skin and the mucous of the eyes. The inventors further found that when a specific cationic polymer was used as the polymer, the composition exhibited, in addition to the above characteristics, an excellent smooth feeling during washing and rinsing, giving favorable soft finishing. Furthermore, the inventors found that when a specific type of nonionic polymer was used as the polymer, the composition produced fine creamy foam ensuring freely control of viscosity of the shampoo composition.

SUMMARY OF THE INVENTION

Accordingly, an object of this invention is to provide a shampoo composition comprising:

(A) one or more amidoamine-type amphoteric surface active agents represented by formula (I) or (II):

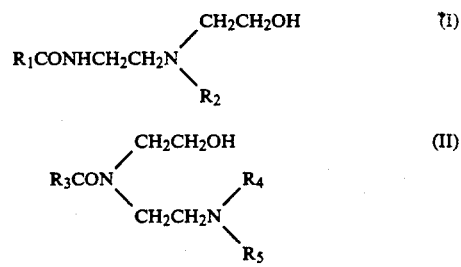

wherein $R_1$ and $R_3$ each independently represent a saturated or unsaturated hydrocarbon group having 7 to 19 carbon atoms, $R_2$ and $R_4$ each independently represent a group $-CH_2COOM_1$, $-CH_2CH_2COOM_1$, or

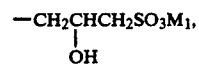

wherein $M_1$ stands for a hydrogen atom, an alkali metal, or an alkanol amine, $R_5$ represents a hydrogen atom, a group $-CH_2COOM_1$, $-CH_2CH_2COOM_1$, or

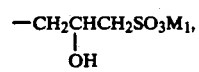

wherein $M_1$ has the same meaning as defined above, (B) a modified silicone polymeric compound containing in a molecule at least one aminoalkyl group and at least one group selected from hydroxyl, hydroxyalkyl, oxyalkylene, and polyoxyalkylene groups, and (C) one or more compounds selected from water-soluble cationic polymers containing an amino group or an ammonium group which is bonded to the polymer chain and water-soluble cationic polymers containing at least dimethyldiallylammonium halide as its constituent unit.

Another object of the present invention is to provide a shampoo composition comprising:

(A) one or more amidoamine-type amphoteric surface active agents represented by formula (I) or (II):

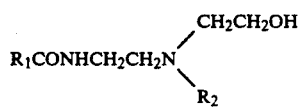

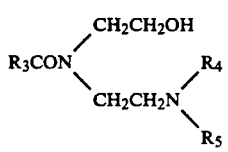

wherein $R_1$ and $R_3$ each independently represent a saturated or unsaturated hydrocarbon group having 7 to 19 carbon atoms, $R_2$ and $R_4$ each independently represent a group $—CH_2COOM_1$, $—CH_2CH_2COOM_1$, or

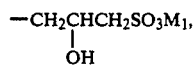

wherein $M_1$ stands for a hydrogen atom, an alkali metal, or an alkanol amine, $R_5$ represents a hydrogen atom, a group $—CH_2COOM_1$, $—CH_2CH_2COOM_1$, or

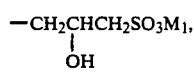

wherein $M_1$ has the same meaning as defined above, (B) a modified silicone polymeric compound containing in a molecule at least one aminoalkyl group and at least one group selected from hydroxyl, hydroxyalkyl, oxyalkylene, and polyoxyalkylene groups, and (D) one or more nonionic polymer Other objects, features and advantages of the invention will hereinafter become more readily apparent from the following description.

DETAILED DESCRIPTION OF THE INVENTION AND PREFERRED EMBODIMENTS

Among amido-amine type amphoteric surface active agents represented by formula (I) or (II), those having linear or branched alkyl or alkenyl groups of $C_7$ to $C_{19}$ for $R_1$ and $R_3$, which generically represent saturated or unsaturated hydrocarbon groups having 7 to 19 carbon atoms, are preferable. Those having linear or branched alkyl groups of $C_7$ to $C_{19}$ for $R_1$ and $R_3$ are particularly preferable.

Specific examples of suitable amido-amine type surface active agents represented by the formula (I) include:

N-lauroyl-N'-carboxymethyl-N'-(2-hydroxyethyl)ethylenediamine,
N-lauroyl-N'-carboxyethyl-N'-(2-hydroxyethyl)ethylenediamine,
N-myristoyl-N'-carboxymethyl-N'-(2-hydroxyethyl)ethylenediamine,
N-myristoyl-N'-carboxyethyl-N'-(2-hydroxyethyl)ethylenediamine,
N-palmitoyl-N'-carboxymethyl-N'-(2-hydroxyethyl)ethylenediamine,
N-palmitoyl-N'-carboxyethyl-N'-(2-hydroxyethyl)ethylenediamine,
and the like as well as their salts. Given as specific examples of suitable amido-amine type surface active agents represented by the formula (II), are:
N-lauroyl-N-(2-hydroxyethyl)-N'-carboxymethylethylenediamine,
N-lauroyl-N-(2-hydroxyethyl)-N',N'-bis(carboxymethyl)ethylenediamine,
N-lauroyl-N-(2-hydroxyethyl)-N',N'-bis(carboxyethyl)ethylenediamine,
N-myristoyl-N-(2-hydroxyethyl)-N'-carboxymethylethylenediamine,
N-myristoyl-N-(2-hydroxyethyl)-N',N'-bis(carboxymethyl)ethylenediamine,
N-myristoyl-N-(2-hydroxyethyl)-N,,N'-bis(carboxyethyl)-ethylenediamine,
N-palmitoyl-N-(2-hydroxyethyl)-N'-carboxymethylethylenediamine,
N-palmitoyl-N-(2-hydroxyethyl)-N',N'-bis(carboxymethyl)ethylenediamine,
N-palmitoyl-N-(2-hydroxyethyl)-N',N'-bis(carboxyethyl)ethylenediamine,
and the like as well as their salts.

Given as salts of these compounds are alkali metal salts such as sodium salt, alkali earth metal salt such as magnesium salt, alkanol amine salt such as triethanolamine salt, and the like.

When these types of salts are used, the surface active agent tends to contain inorganic salts as contaminants. It is desirable to use desalted amido-amine type surface active agents from which all or a portion of such inorganic salts is removed so that the content of the inorganic salt contaminants in the final detergent composition be less than 1% by weight.

Desalted amido-amine type surface active agents can be prepared by solvent extraction, electrodialysis, or the like. A particularly preferable amido-amine type surface active agent can be prepared by converting a secondary amido-amino acid of the following formula (Ia) into a triethanolamine salt and desalting the resulting product to make its salt contaminant concentration 1%.

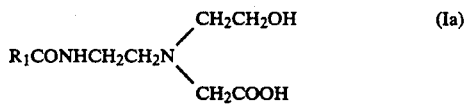

Such a desalted amido-amine type surface active agent can easily dissolve polymers which are soluble in water but insoluble in concentrated inorganic salt solutions. Here, polymers which ar soluble in water but insoluble in concentrated inorganic salt solutions include cationic polymers exhibiting conditioning effects to the skin and hair fibers such as cationic cellulose, cationic starch, cationic natural gums, diallyl quaternary ammonium salt homopolymers, and the like; anionic polymers providing a viscosity increasing effect such as carboxymethyl cellulose, carboxyvinyl polymer, and the like; and nonionic polymers promoting a viscosity increasing effect as well as tactile improvement effect to the skin and the hair such as hydroxyethyl cellulose, polyvinyl alcohol, polyvinylpyrrolidone, polyethylene oxide, and the like.

Amido-amine type surface active agents, component (A), can be prepared, for example, by the method described in Japanese Patent Application Laid-open No. 115512/1985. Such amido-amine type surface active agents can be used independently or two or more of them can be used in combination, in an amount of 1-40% by weight, preferably 5-30% by weight, in the composition of the present invention.

Modified silicone polymeric compounds of any molecular structure, e.g. branched, linear, and netting types, can be used as component (B) so long as the same contain in their molecules at least one aminoalkyl group and at least one group selected from hydroxyl, hydroxyalkyl, oxyalkylene, and polyoxyalkylene groups. Organopolysiloxanes which construct the modified silicone polymeric compounds may include, in addition to the above groups, alkyl groups, e.g. methyl, ethyl, propyl; alkenyl groups, e.g. allyl; aryl groups, e.g. phenyl, naphthyl; cycloalkyl groups, e.g. cyclohexyl; and the like. Those containing methyl group are commonly used.

A typical aminoalkyl group contained in modified silicone polymeric compounds is that shown by the following formula.

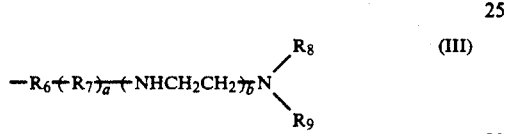
(III)

wherein $R_6$ represents a divalent hydrocarbon group, $R_7$ represents a group $-OCH_2CH_2-$,

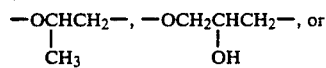

$R_8$ and $R_9$ are individually a hydrogen or a monovalent hydrocarbon group, and a and b denote integers of 1-6.

As divalent hydrocarbon groups represented by $R_6$, alkylene groups, e.g. methylene, ethylene, propylene, butylene, $-CH_2(CH_3)CH_2-$; and alkylene-arylene groups, e.g. $-(CH_2)_2-C_6H_4-$, are given. Of these groups, alkylene groups, particularly propylene group, are preferable. Alkyl groups, e.g. methyl, ethyl, propyl, hexyl; and phenyl group are given as examples of monovalent hydrocarbon groups represented by $R_8$ and $R_9$. Both $R_8$ and $R_9$ may be hydrogen atoms, or both may be monovalent hydrocarbon groups, or either one of $R_8$ and $R_9$ is a hydrogen, with the other being a monovalent hydrocarbon group. A preferable value for a and b is 1.

A typical hydroxyalkyl group which is another group to be contained in the modified silicone polymeric compound molecule is that shown by following formula (IV).

$-R_6OH$ (IV)

wherein $-R_6$ has the same meaning as defined above.

Oxyalkylene and polyoxyalkylene groups are typified by the groups shown by following formula (V).

$-(-R_6-)_c-O-(C_3H_2O)_3-H$ (V)

wherein $-R_6$ has the same meaning as defined above, c represent 0 or 1, d denotes an integer of 1-100, and e is indicates an integer of 1-5.

Of the hydroxyalkyl groups represented by formula (V), those in which c=1, d=3 to 70, and e=2 or 3 are preferable. A hydroxyalkyl group produced by random or block bond of a group having the value e=2 and a group having the value e=3 is acceptable. This applies to the cases where e is other than 2 or 3.

Typical modified silicone polymeric compounds are those represented by formulae (VI) and (VII).

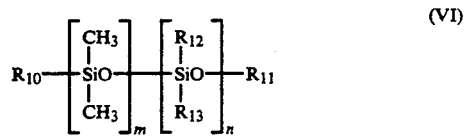
(VI)

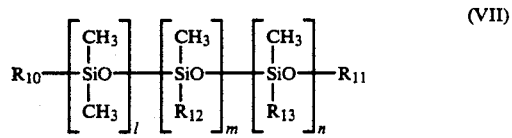
(VII)

wherein $R_{10}$ is a methyl or hydroxy group, and $R_{11}$ is a methyl group or a hydrogen, $R_{12}$ is above-mentioned aminoalkyl group (III), $R_{13}$ is a hydroxy, hydroxyalkyl, oxyalkylene, or polyoxyalkylene group, and l, m and n are integers dependent on the molecular weight.

Of these, particularly preferable modified silicone polymeric compounds are those represented by formula (VIII).

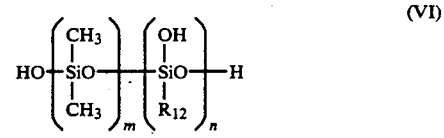
(VI)

wherein $R_{12}$ is above-mentioned aminoalkyl group (III), and l, m and n are integers dependent on the molecular weight.

One of the specific examples of modified silicone polymeric compounds is that described in Cosmetic Ingredient Dictionary, third edition, in the name of Amodimethicone. This is represented by formula (IX) and has average molecular weight of 3,000 to 100,000.

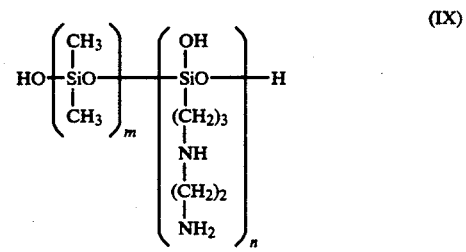
(IX)

wherein m and n are integers dependent on the molecular weight.

It is desirable that the modified silicone polymeric compounds of the present invention be used in a form of aqueous emulsion. Such a emulsion can be obtained by emulsifying, in the presence of a quartenary ammonium salt surfactant and water, a cyclic diorganopolysiloxane and an organodialkoxysilane having an aminoalkyl group and at least one group selected from hydroxyl, hydroxyalkyl, oxyalkylene, polyoxyalkylene groups, according to the process described, for example, in Japanese Patent Application Laid-open No. 38609/1981.

When the modified silicone polymeric compounds is used in a form of aqueous emulsion, the amount of modified silicone polymeric compounds in the emulsion is usually 20-60% by weight, and preferably 30-50% by weight.

Given as examples of commercial modified silicone polymer emulsions which can be suitably used in this invention are SM 8702C (tradename, product of Toray Silicone Co.) and DC 929 (tradename, product of Dow Corning Co.).

Component (B) is used in an amount of 0.005-0.3% by weight, and preferably 0.01-0.25% by weight, in the composition of the present invention. When component (B) is in a form of an aqueous emulsion, the amount of the aqueous emulsion incorporated into the composition of the present invention is 0.01-0.5% by weight, and preferably 0.05-0.4% by weight.

Cationic polymers used in this invention as component (C) are (i) water-soluble polymers containing an amino group or an ammonium group which is bonded to the polymer chain or (ii) water-soluble polymers containing at least dimethyldiallylammonium halide as its constituent unit. Examples of these polymers include cationized cellulose derivatives, cationic starch, cationic natural gums, copolymers of diallyl quaternary ammonium salt and acrylamide, quaternarized polyvinylpyrrolidone derivatives, and the like.

A compound of following formula (X) is given as an example of preferred cationized cellulose derivatives:

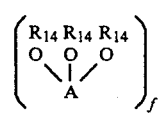
(X)

wherein A represents an anhydrous glucose unit residue, f denotes an integer of 50 to 20,000, and each $R_{14}$ individually represents a group represented by the following formula (XI):

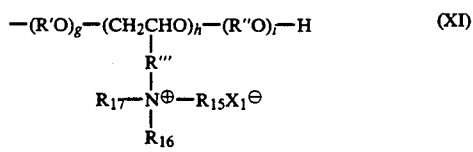
(XI)

wherein R' and R" individually represent an alkylene group having 2 or 3 carbon atoms, g is an integer of 0 to 10, h is an integer of 0 to 3, i is an integer of 0 to 10, R''' represents an alkylene group or a hydroxyalkylene group each having 1 to 3 carbon atoms, $R_{15}$, $R_{16}$, and $R_{17}$ may be the same or different and represent alkyl groups, aryl groups, aralkyl groups, each having not more than 10 carbon atoms, or may form a heterocycle together with the nitrogen atom, and $X_1$ represents an anion, e.g. chlorine, bromine, iodine, sulfuric acid, sulfonic acid, methyl sulfate, phosphoric acid, nitric acid, and the like.

A preferable range of the cation substitution degree in cationized cellulose is 0.01 to 1, i.e., in terms of the average value of h for anhydrous glucose 0.01 to 1, and preferably 0.02 to 0.5. The average of g plus i is 1 to 3. A substitution degree of below 0.01 is not sufficient. The value not more than 1 is preferable from the aspect of the reaction yield, although the value above 1 can be acceptable. The molecular weight of the cationic cellulose used is between 100,000 and 3,000,000.

The compounds represented by the following formula (XII) are preferable cationic starches.

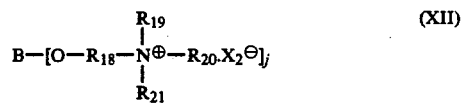
(XII)

wherein B represents a starch residual group, $R_{18}$ represents an alkylene group or a hydroxyalkylene group, $R_{19}$, $R_{20}$, and $R_{21}$ may be the same or different and represent alkyl groups, aryl groups, aralkyl groups, each having not more than 10 carbon atoms, or may form a heterocycle together with the u nitrogen atom, $X_2$ represents an anion, e.g. chlorine, bromine, iodine, sulfuric acid, sulfonic acid, methyl sulfate, phosphoric acid, nitric acid, and the like, and j is a positive integer.

A preferable range of the cation substitution degree of cationic starch is 0.01 to 1. Specifically, cationic starches having 0.01 to 1, preferably 0.02 to 0.5, cationic group per anhydrous glucose unit are desirable. A substitution degree of below 0.01 is not sufficient. The value not more than 1 is preferable from the aspect of the reaction yield, although the value above 1 can be acceptable.

A preferable cationized guarh-gum derivative is that

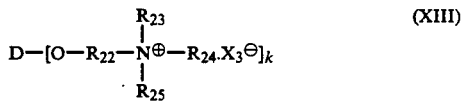
(XIII)

wherein D represents a guarh-gum residual group, $R_{22}$ represents a alkylene group or a hydroxyalkylene group, $R_{23}$, $R_{24}$, and $R_{25}$ may be the same or different and represent alkyl groups, aryl groups, aralkyl groups, each having not more than 10 carbon atoms, or may form a heterocycle together with the nitrogen atom, $X_3$ represents an anion, e.g. chlorine, bromine, iodine, sulfuric acid, sulfonic acid, methyl sulfate, phosphoric acid, nitric acid, and the like, and k is a positive integer.

A preferable range of the cation substitution degree of cationic starch is 0.01 to 1. Specifically, cationic guarh-gum derivatives having 0.01 to 1, preferably 0.02 to 0.5, cationic group per sugar unit are desirable. This type of cationic polymers is described in Japanese Patent Publication Nos. 35640/1983 and 46158/1985, and Japanese Patent Application Laid-open No. 53996/1983, and is commercially available in the tradename of Jagual (product of Cellanease Stein-Hohl Co.).

The compounds represented by the following formula (VIII) or (IX) are preferable as a cationic diallyl quaternary ammonium salt/acryl amide copolymer.

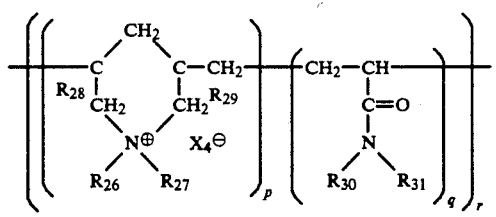

(XIV)

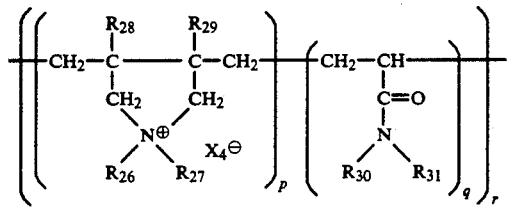

(XV)

wherein $R_{26}$ and $R_{27}$ may be the same or different and represent hydrogen atoms, alkyl groups having 1 to 18 carbon atoms, phenyl groups, aryl groups, hydroxyalkyl groups, amidealkyl groups, cyanoalkyl groups, alkoxyalkyl groups, or carboalkoxyalkyl groups, $R_{28}$, $R_{29}$, $R_{30}$, and $R_{31}$ may be the same or different and represent hydrogen atoms, lower alkyl groups having 1 to 3 carbon atoms, or phenyl groups, $X_4$ represents an anion, e.g. chlorine, bromine, iodine, sulfuric acid, sulfonic acid, methyl sulfate, nitric acid, and the like, p is an integer of 1 to 50, q is an integer of to 50, and r is an integer of 150 to 8,000.

The molecular weight of a diallyl quaternary ammonium salt/acryl amide copolymer is in the range of 30,000 to 2,000,000, and preferably of 100,000 to 1,000,000.

Compounds represented by the following formula (XVI) are preferable as a quaternarized polyvinylpyrrolidone derivative.

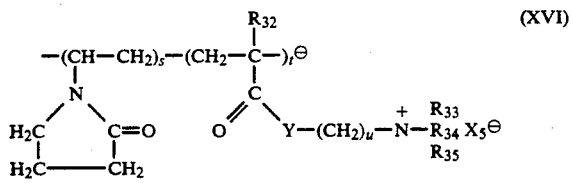

(XVI)

wherein $R_{32}$ represents a hydrogen atom or a lower alkyl group having 1 to 3 carbon atoms, $R_{33}$, $R_{34}$, and $R_{35}$ may be the same or different and represent hydrogen atoms, alkyl groups having 1 to 4 carbon atoms, hydroxyalkyl groups, amidealkyl groups, cyanoalkyl groups, alkoxyalkyl groups, or carboalkoxyalkyl groups, Y represents an oxygen atom or the NH group of an amide bond, $X_5$ represents an anion, e.g. chlorine, bromine, iodine, sulfuric acid, sulfonic acid, alkyl sulfate of a $C_{1-4}$ carbon atom content, phosphoric acid, nitric acid, and the like, u is an integer of 1 to 10, s and t are integers satisfying $s+t=20$ to 8,000.

A molecular weight of a quaternarized polyvinylpyrrolidone derivative is between 10,000 and 2,000,000, with the particularly preferable range being between 50,000 and 1,500,000.

The content of the cationic nitrogen originating from cationic polymers in the above vinyl polymers is 0.004 to 0.2%, and preferably 0.01 to 0.15% of the vinyl polymers. A sufficient effect cannot be expected from the nitrogen atom content of less than 0.004%. On the other hand, the content of above 0.2% causes the vinyl polymer becoming colored and is disadvantageous in view of economy, even though a good performance can be obtained.

The above cationic polymers are incorporated into the composition of the present invention as component C either independently or in combination in an amount of 0.01 to 2% by weight, and preferably 0.1 to 0.8% by weight Following examples are given as prefereable nonionic polymer, component (D), of the present invention (1) Cellulose derivatives

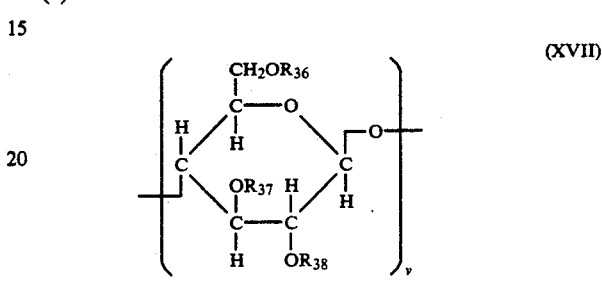

(XVII)

wherein $R_{36}$, $R_{37}$, and $R_{38}$ may be the same or different and represent a hydrogen atom, a group $-(-CH_2CH_2O-)_2-$, wherein w is a number 1-5, $-CH_3$, or $-C_3H_6OH$; and v is a number 50-500.

Specific examples include hydroxyethyl cellulose, hydroxypropyl cellulose, hydroxypropylmethyl cellulose, methyl cellulose, and the like.

Of these, hydroxyethyl cellulose are commercially available in the tradenames of Cellosize (product of UCC), Natrosol (product of Hercules Corp.), and the like. For the purpose of the present invention those having 1.0–4.0, preferably 1.8–3.0, moles of ethylene oxide added per glucose residue are suitable.

Other commercially available products are Viscontran MC (methyl cellulose, product of Henkel Co.), Klucel (hydroxypropy cellulose, product of Hercules Corp.), Metholose (hydroxypropylmethyl cellulose, product of Shinetsu Chemical Co.), Viscontran MHPC (hydroxypropylmethyl cellulose, product of Henkel Co.), and the like. In these methyl cellulose, those containing 10–40%, preferably 20–30%, of methoxy group and 1–20%, preferably 5–15%, of hydropropoxy group are suitable.

(2) Polyvinyl alcohol derivatives
(3) Polyvinylalkyl ether derivatives
(4) Polyethylene oxide derivatives The above nonionic polymers are incorporated into the composition of the present invention as component D either independently or in combination in an amount of 0.01 to 3% by weight, and preferably 0.1 to 2% by weight.

The shampoo composition of the present invention can be prepared according to a conventional method by using components (A), (B), and (C), or components (A), (B), and (D). Both types exhibit an excellent conditioning effect and are only slight irritative. When the cationic polymer of component (C) is used, the composition gives exceptionally goof feeling during washing and rinsing, and softly finished air after drying. When the nonionic polymer of component (D) is used, the composition which can produce creamy foam can be obtained.

Viscosity of shampoos can be freely controlled by using such a composition.

When one or more quaternary branched ammonium salts represented by following formula (XVIII) or (XIX) are used together with the above components, the composition exhibits improved softness and smoothness, as well as even better conditioning effects.

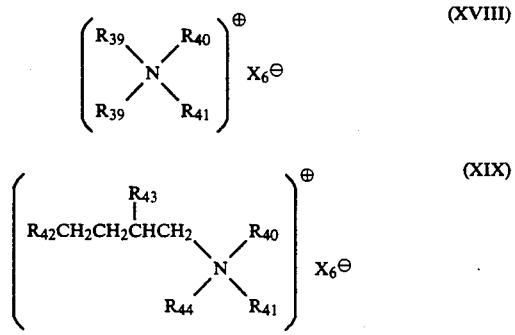

wherein $R_{39}$ represents a mixture of (a) a branched alkyl group represented by

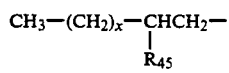

and (b) a linear alkyl group represented by $CH_3-(CH_2)_y-$ (wherein $R_{45}$ represents a methyl or ethyl group, x is an integer to make the carbon atom content of the branched alkyl group 8 to 16, and y is an integer of 7 to 15), with a ratio (a)/(a)+(b) being 0.1 to 1, $R_{40}$ and $R_{41}$ independently represent a benzyl group, an alkyl group having 1 to 3 carbon atoms, or a hydroxyalkyl group having 1 to 3 carbon atoms, $R_{42}$ and $R_{43}$ independently represent an alkyl group having 2 to 12 carbon atoms, $R_{44}$ represents a group

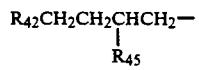

or an alkyl group having 1 to 3 carbon atoms, and $X_6^-$ represents a halogen ion or an organic anion.

Specific examples of particularly preferable branched quaternary ammonium salts represented by formula (XVIII) are dialkyldimethylammonium chloride in which the alkyl group $R_{39}$ has 8 to 16 carbon atoms and a branched ratio is 0.1 to 0.5. Given as preferable examples of this branched quaternary ammonium salt of formula (XIX) are 2-decyltetradecyltrimethylammonium chloride, 2-dodecylhexadecyltrimethylammonium chloride, di-2-hexyldecyldimethylammonium chloride, di-2-octyldodecylammonium chloride, and the like.

Besides the above two essential components, various components commonly known for use in a shampoo composition can be formulated to the extent that the effects of the present invention is not adversely affected. Such optional components include, for example, foaming promoters, e.g. anionic, amphoteric, and nonionic surface active agents; tactile improvers, e.g. salts of higher fatty acid, alkylamine oxides, fatty acid alkanol amide, squalane, lanoline; moisturizing agents, e.g. propylene glycol, glycerin, diethylene glycol, monoethyl ether, sorbitol; viscosity adjustment agents, e.g. methyl cellulose, carboxyvinyl polymer, hydroxyethyl cellulose, polyoxyethylene glycol distearate, ethanol; pearling agents, perfumes, coloring agents, UV absorbers, antioxidants, antiseptics, e.g. triclosan, trichlorocarbanilide; antiinflammation agents, e.g. potassium glytylphosphate, tochopheryl acetate; antidandruff agents, e.g. zinc pyrition, oxtopirox; preservatives, e.g. methyl paraben, butyl paraben; and the like.

The problem due to secondary amidoamio acids and their salts in shampoo compositions, i.e., poor conditioning effects, such as uneasy finger passage through the hair both in dry and wet conditions and poor feeling to the touch, have been improved by the present invention. Furthermore, the composition of the present invention provides foam with improved quality and makes viscosity control easy. It can be directed to products requiring lower irritation to the skin and the mucosa, e.g. shampoos for babies, for persons having delicate, sensitive skin, for people who frequently wash hair, and the like. It can also suitably be used for the hair suffering from bad finger or comb passage due to perm treatment, for the hair which can be set only with difficulty.

Other features of the invention will become apparent in the course of the following description of the exemplary embodiments which are given for illustration of the invention and are not intended to be limiting thereof.

EXAMPLES

Example 1

Shampoo compositions were prepared according to the formulations listed in Tables 1 to 3. Each composition was tested in terms of its feeling (sensory evaluation) and the irritation to the skin, during washing, rinsing, after drying with towel, after air-drying.

In the sensory evaluation, 1 g of sample composition was applied to a bundle of hair (weight: 20 g, length: 15 cm) of a healthy Japanese woman. Feeling to the touch when the shampoo was foamed for 1 minute; finger passage through the hair during rinsing; finger passage through the hair and stickiness after drying with towel; and stickiness, hair-set easiness, and passage of comb through the hair after drying with dryer were evaluated by 5 expert panelists according to the following standards. The irritation of the skin was evaluated by washing the skin of guinea pigs seven times with a 25% solution of the shampoo composition. Shampoo compositions to which a nonionic polymer was added were also evaluated with respect to the solubility of the polymer and the quality of the foam.

Evaluation Standard

Feeling to the touch during washing:
  AAA: Soft and smooth, fingers pass through very easily
  BBB: Smooth, fingers pass through easily
  CCC: Hair is not slippery, fingers pass through with difficulty
  DDD: Hair feels creaky and tangles
Passage of finger through the hair:
  AAA: Hair gives no creaky feeling at all, fingers pass through very easily
  BBB: Hair gives only slight creaky feeling, fingers pass through easily
  CCC: Hair gives rather strong creaky feeling, fingers pass through with difficulty DDD: Hair gives strong creaky feeling, fingers do not pass through easily Stickiness:
AAA: Hair is not sticky but sleek
BBB: Hair is slightly sticky
CCC: Hair is sticky Softness:
AAA: Hair is very soft and pliable
BBB: Hair is soft
CCC: Hair is a little devoid softness
DDD: Hair is stiff Hair-setup performance:
AAA: Hair is naturally setup
BBB: Setup is not always complete
CCC: Setup is incomplete with many hair-flies Passage of comb:
AAA: Hair is smooth providing good passage of comb
BBB: Comb passage is slightly braked
CCC: Comb does not easily go through the hair Irritation to the skin:
AAA: Irritation is very low
BBB: Slightly irritative
CCC: Irritation is rather strong Solubility of nonionic polymer:
AAA: 1% of nonionic polymer added makes a transparent solution at room temperature
BBB: 1% of nonionic polymer added resulted in a slightly turbid solution at room temperature
CCC: 1% of nonionic polymer added resulted in a turbid solution or formed precipitate at room temperature Quality of foam:
AAA: Foam is creamy
BBB: Foam is slightly creamy
BBB: Foam is rough

TABLE 2

| | Invention Compositions | | | | |
|---|---|---|---|---|---|
| | 7 | 8 | 9 | 10 | 11 |
| N-lauroyl-N'-carboxymethyl-N'-(2-hydroxyethyl)ethylenediamine triethanolamine | 18 | 18 | 18 | 18 | 18 |
| Cationized polymer 1 *1 | 0.1 | 0.5 | — | — | — |
| Cationized polymer 2 *2 | — | — | 0.5 | — | — |
| Cationized polymer 3 *3 | — | — | — | 0.5 | — |
| Cationized polymer 4 *4 | — | — | — | — | 0.5 |
| Modified silicone aqueous emulsion *5 | 0.3 | 0.3 | 0.3 | 0.3 | 0.3 |
| Purified water | Balance | Balance | Balance | Balance | Balance |
| Feeling during washing | AAA | AAA | AAA | AAA | AAA |
| Finger passage during rinsing | AAA | AAA | AAA | AAA | AAA |
| Finger passage after drying with towel | AAA | AAA | AAA | AAA | AAA |
| Stickiness after drying with towel | AAA | AAA | AAA | AAA | AAA |
| Softness after drying with towel | BBB | AAA | AAA | AAA | AAA |
| Stickiness after drying with dryer | AAA | AAA | AAA | AAA | AAA |
| Hair-set after drying with dryer | AAA | AAA | AAA | AAA | AAA |
| Comb passage after drying with dryer | AAA | AAA | AAA | AAA | AAA |
| Irritation to the skin | AAA | AAA | AAA | AAA | AAA |

*1 Polymer JR-400 (Tradename: cationized cellulose, product of UCC)
*2 Cationized corn starch, cationized degree: 0.3
*3 Marcoat 550 (Tradename: copolymer of N,N-dimethyl-3,5-methylenepiperidinium chloride and acrylamide, product of Merck Co.)
*4 Gafcoat 755N (Tradename: quarternarized ethyl sulfate of vinyl-pyrroridone dimethylaminoacrylate copolymer, product of Guff Corp.)
*5 DC 929 (Tradename: modified silicone polymer, containing 35% Amodimethicone, product of Dow Corning).

TABLE 1

| | Comparative Compositions | | | | Invention Compositions | | | | | |
|---|---|---|---|---|---|---|---|---|---|---|
| | 1 | 2 | 3 | 4 | 1 | 2 | 3 | 4 | 5 | 6 |
| Sodium N-lauroyl-N'-carboxymethyl-N'-(2-hydroxyethyl)ethylenediamine | 16 | — | 15 | — | 15 | — | 15 | 15 | 15 | 15 |
| Sodium N-lauroyl-N-(2-hydroxyethyl)-N',N'-bis(carboxymethyl)ethylenediamine | — | 15 | — | 15 | — | 15 | — | — | — | — |
| Cationized polymer *1 | — | — | 1.0 | 1.0 | 0.5 | 0.5 | 0.5 | 0.5 | 0.5 | 0.5 |
| Modified silicone aqueous emulsion *2 | — | — | — | — | 0.1 | 0.1 | 0.01 | 0.05 | 0.4 | 0.5 |
| Purified water | Balance | Balance | Balance | Balance | Balance | Balance | Balance | Balance | Balance | Balance |
| Feeling during washing | DDD | DDD | BBB | BBB | AAA | AAA | BBB | BBB | AAA | AAA |
| Finger passage during rinsing | DDD | DDD | AAA | AAA | AAA | AAA | BBB | BBB | AAA | AAA |
| Finger passage after drying with towel | DDD | DDD | BBB | BBB | AAA | AAA | BBB | BBB | AAA | AAA |
| Stickiness after drying with towel | AAA | AAA | CCC | CCC | AAA | AAA | AAA | AAA | AAA | AAA |
| Stickiness after drying with dryer | AAA | AAA | CCC | CCC | AAA | AAA | AAA | AAA | AAA | AAA |
| Hair-set after drying with dryer | CCC | CCC | BBB | BBB | AAA | AAA | AAA | AAA | AAA | AAA |
| Comb passage after drying with dryer | CCC | CCC | BBB | BBB | AAA | AAA | AAA | AAA | AAA | AAA |
| Irritation to the skin | AAA | AAA | AAA | AAA | AAA | AAA | AAA | AAA | AAA | AAA |

*1 Polymer JR-400 (Tradename: cationized cellulose, product of UCC)
*2 DC 929 (Tradename: modified silicone polymer, containing 35% Amodimethicone, product of Dow Corning.

TABLE 3

| | Comparative Compositions | | | Invention Compositions | | | | | |
|---|---|---|---|---|---|---|---|---|---|
| | 5 | 6 | 7 | 12 | 13 | 14 | 15 | 16 | 17 |
| 2-Lauryl-N-carboxymethyl-N-hydroxyimidazolinium betaine *1 | 18 | 18 | — | — | — | — | — | — | — |
| N-lauroyl-N'-carboxymethyl-N'-(2-hydroxyethyl)ethylenediamine triethanolamine | — | — | 18 | 18 | 18 | 18 | 18 | 18 | 18 |
| Nonionic polymer *2 | 0.8 | — | — | — | — | — | — | 2.0 | 0.5 |
| Nonionic polymer *3 | — | 0.5 | — | 0.1 | 0.2 | 0.8 | 2.0 | — | — |
| Modified silicone aqueous emulsion *4 | 0.2 | 0.2 | 0.2 | 0.2 | 0.2 | 0.2 | 0.2 | 0.2 | 0.2 |
| Purified water | Balance | Balance | Balance | Balance | Balance | Balance | Balance | Balance | Balance |
| Feeling during washing | BBB | BBB | BBB | BBB | BBB | BBB | BBB | BBB | BBB |
| Quality of foam | BBB | BBB | CCC | AAA | AAA | AAA | AAA | AAA | AAA |
| Irritation to the skin | AAA | AAA | AAA | AAA | AAA | AAA | AAA | AAA | AAA |
| Solubility of polymer | CCC | CCC | — | AAA | AAA | AAA | AAA | AAA | AAA |

*1 Softazolin CH: Tradename, compound having the following structure manufactured by Kawaken Fine Chemical Co.

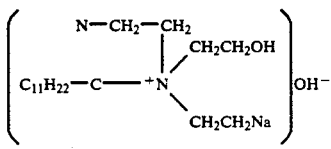

*2 Metholose 60SH50 (product of Shin-etsu Chemical Co.)
*3 LA-18 (polyvinyl alcohol, product of Shin-etsu Chemical Co.)
*4 SM 8702C (Tradename: modified silicone polymer, containing 40% Amodimethicone, product of Toray Silicone Co.

As evidenced by the above evaluation results, the shampoo composition of the present invention exhibits excellent passage of finger through the hair under both wet and dry conditions, superb feeling uopn use, good hair-set effects. The composition dissolve ionic polymers well and produced foam with good quality. Its viscosity can easily be controlled.

EXAMPLES 2-4

All shampoo compositions having formulations of Examples 2-4 were very mild to the skin with little irritation and exhibited excellent conditioning effects.

| Example 2 | % by weight |
|---|---|
| Ammonium N-lauroyl-N'-carboxymethyl-N'-(2-hydroxyethyl)ethylenediamine | 12 |
| Sodium polyoxyethylene (EO = 3.0) laurylether sulfate | 5 |
| Lauric acid diethanolamide | 3 |
| Cationic polymer (Marcoat 100, Merck Co.) | 0.2 |
| Modified silicone aqueous suspension (SM 8702C, Toray Silicone Co.) | 0.07 |
| Antiseptic | 0.1 |
| Perfume, Colorant | Appropriate amount |
| Water | Balance |

| Example 3 | % by weight |
|---|---|
| N-lauroyl-N'-carboxymethyl-N'-(2-hydroxyethyl)ethylenediamine triethanolamine | 18 |
| Lauryldimethylaminoacetic acid betaine | 3 |
| 2-Decyltetradecyltrimethylammonium chloride | 0.3 |
| Modified silicone aqueous suspension (DC-929, Dow Corning Co.) | 0.05 |
| Metholose 60SH400 (Shin-etsu Chemical Co.) | 1.0 |
| Antiseptic | 0.1 |
| Perfume, Colorant | Appropriate |

*Example 3 -continued*

| Example 3 | % by weight |
|---|---|
| | amount |
| Water | Balance |

| Example 4 | % by weight |
|---|---|
| N-lauroyl-N'-carboxymethyl-N'-(2-hydroxyethyl)ethylenediamine triethanolamine | 15 |
| Laurylamine oxide | 5 |
| Cationic polymer (Polymer JR-400, product of UCC) | 0.2 |
| Pylactoneohramine (octopirox) | 1.0 |
| Modified silicone aqueous suspension (SM 8702C, Toray Silicone Co.) | 0.2 |
| Polyvinyl alcohol | 0.5 |
| Laurylamidopropyldimethylaminoacetic acid betaine | 1.0 |
| Antiseptic | 0.1 |
| Perfume, Colorant | Appropriate amount |
| Water | Balance |

Obviously, numerous modifications and variations of the present invention are possible in light of the above teachings. It is therefore to be understood that within the scope of the appended claims, the invention may be practiced otherwise than as specifically described herein.

What is claimed is:

1. An aqueous shampoo composition, comprising:
   (A) 1-40% by weight of at least one amidoamine amphoteric surface active agent having the formula (I) or (II):

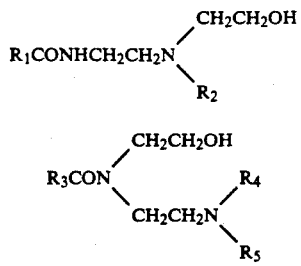

(I)

(II)

wherein $R_1$ and $R_3$ each independently represents a saturated or unsaturated hydrocarbon group having 7 to 19 carbon atoms, $R_2$ and $R_4$ each independently represents a group:

$-CH_2COOM_1$, $-CH_2CH_2COOM_1$, or $-CH_2CHCH_2SO_3M_1$,
$\phantom{-CH_2CH_2COOM_1, \text{or} -CH_2CH}$ $|$
$\phantom{-CH_2CH_2COOM_1, \text{or} -CH_2CH}$ OH wherein $M_1$ is a hydrogen atom, an alkali metal, an alkanolamine, and $R_5$ represents a hydrogen atom, $-CH_2COOM_1$, $-CH_2CH_2COOM_1$, or $-CH_2CHCH_2SCM_1$,
$\phantom{-CH_2CH}$ $|$
$\phantom{-CH_2CH}$ OH wherein $M_1$ has the same meaning as defined above;
(B) 0.005–0.3% by weight of a modified silicone polymeric compound having the formula (VI) or (VII):

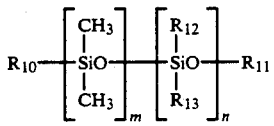

(VI)

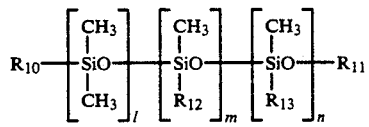

(VII)

wherein $R_{10}$ is a methyl group or a hydroxy group, $R_{11}$ is a methyl group or a hydrogen atom, $R_{12}$ is an aminoalkyl group of the formula (III):

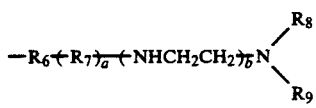

(III)

wherein $R_6$ represents a divalent hydrocarbon group, $R_7$ represents $-OCH_2CH_2-$, $-OCHCH_2-$, $-OCH_2CHCH_2-$ or $-OCH_2-CH-$,
$\phantom{-O}|$ $\phantom{-OCH_2}|$ $\phantom{-OCH_2-C}|$
$\phantom{-O}CH_3$ $\phantom{-OCH_2}OH$ $\phantom{-OCH_2-C}CH_2OH$ $R_8$ and $R_9$ are individually a hydrogen atom or a monovalent hydrocarbon group, and a and b denote integers of 1–6, $R_{13}$ is a hydroxy group, a hydroxyalkyl group, an oxyalkylene group or a polyoxyalkylene group, and l, m and n are integers depending on the molecular weight; and (C) 0.01–3% by weight of at least one nonionic polymer.

2. The aqueous shampoo composition of claim 1, wherein said at least one nonionic polymer is a water-soluble polymer containing an amino group, or an ammonium group which is bonded to the polymer chain or a water-soluble polymer containing at least dimethyldiallylammonium halide as a constituent unit.

3. The aqueous shampoo composition of claim 1, wherein said nonionic polymer is selected from the group consisting of cationized cellulose derivatives, cationic starch, cationic natural gums, copolymers of diallyl quaternary ammonium salt, acrylamide and quaternized polyvinylpyrrolidone derivatives.

4. The aqueous shampoo composition of claim 1, wherein said nonionic polymer is used in the amount of 0.1 to 2% by weight.

5. The aqueous shampoo composition of claim 1, wherein said amidoamine amphoteric surface active agent of the formula (I) is selected from the group consisting of N-lauroyl-N'-carboxymethyl-N'-( 2-hydroxyethyl)ethylenediamine, N-lauroyl-N'-carboxyethyl-N'-(2-hydroxyethyl)ethylenediamine, N-myristoyl-N'-carboxy-N'(2-hydroxyethyl)ethylenediamine, N-myristoyl-N'-carboxyethyl-N'-(2-hydroxyethyl)ethylenediamine, N-palmitoyl-N'-carboxymethyl-N'-(2-hydroxyethyl)ethylenediamine, N-palmitoyl-N'-carboxymethyl-N'-(α-hydroxyethyl)ethylenediamine, and salts thereof.

6. The aqueous shampoo composition of claim 1, wherein said salts are alkali metal salts, alkali earth metal salts or alkanol amine salts.

7. The aqueous shampoo composition of claim 1, wherein said amidoamine amphoteric surface active agent of the formula (II) is selected from the group consisting of N-lauroyl-N-(2-hydroxyethyl)-N'-carboxymethylethylenediamine, N-lauroyl-N-(2-hydroxyethyl)-N',N'-bis(carboxymethyl)ethylenediamine, N-lauroyl-N-(2-hydroxyethyl)-N', N'-bis(carboxyethyl)ethylenediamine, N-myristoyl-N-(2-hydroxyethyl)-N'-carboxymethylethylenediamine, N-myristoyl-N-(2-hydroxyethyl)-N',N'-bis(carboxymethyl)ethylenediamine, N-myristoyl-N-(2-hydroxyethyl)-N',N'-bis(carboxyethyl)ethylenediamine, N-palmitoyl-N-(2-hydroxyethyl)-N'-carboxymethylethylenediamine, N-palmitoyl-N-(2-hydroxyethyl)-N,N'-bis(carboxymethyl) ethylenediamine, N-palmitoyl-N-(2-hydroxyethyl)-N',N'-bis(carboxyethyl)ethylenediame and slats thereof.

8. The aqueous shampoo composition of claim 7, wherein said salts are alkali metal salts, alkali earth metal salts or alkanol amine salts.

9. The aqueous shampoo composition of claim 1, wherein in said modified silicone polymeric compound of the formula (III), b has a value of 1.

10. The aqueous shampoo composition of claim 1, wherein said modified silicone polymeric compound has the formula (IX):

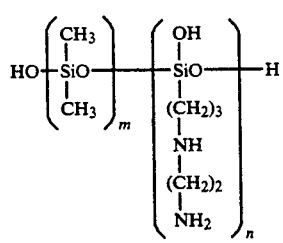
(IX)
wherein m and n are integers such that said compound has a molecular weight of 3,000 to 100,000.
11. The aqueous shampoo composition of claim 1, wherein said modified silicone polymeric compound is used as an aqueous emulsion.
12. The aqueous shampoo composition of claim 1, wherein component (B) is used in an amount of 0.01 to 0.25% by weight.
* * * * *

UNITED STATES PATENT AND TRADEMARK OFFICE
CERTIFICATE OF CORRECTION

PATENT NO. : 5,211,883

DATED : MAY 18, 1993

INVENTOR(S) : SAHOKO YAMASHINA ET AL

It is certified that error appears in the above-indentified patent and that said Letters Patent is hereby corrected as shown below:

Column 6, line 1, "$-(-R_6-)_c-O-(C_3H_2O)_3-H$" should read -- $-(-R_6-)_c-O-(C_eH_{2e}O)_d-H$ --.

Column 6, line 4, "c represent 0 or 1" should read --c represents 0 or 1--.

Column 6, lines 4-5, "e is indicates" should read --e indicates--.

Column 10, lines 27-28, "$(-CH_2C-H_2O-)_2$" should read --$(-CH_2C-H_2O-)_w$"

Column 10, line 63, "only slight irritative" should read --only slightly irritative--.

Column 10, line 65, "goof feeling" should read --good feeling--.

Column 13, line 36, "BBB: Foam is rough" should read --CCC: Foam is rough--.

UNITED STATES PATENT AND TRADEMARK OFFICE
CERTIFICATE OF CORRECTION

PATENT NO. : 5,211,883
DATED : MAY 18, 1993
INVENTOR(S) : SAHOKO YAMASHINA ET AL

It is certified that error appears in the above-indentified patent and that said Letters Patent is hereby corrected as shown below:

Column 13, Table 1 under column 1, "16" should read --15--.

Column 15, line 32, "uopn" should read --upon--.

Column 18, lines 29-30, "N-myristoyl-N'-carboxy-N'(2-hydroxyethyl)ethylene-diamine" should read --N-myristoyl-N'-carboxymethyl-N'-(2-hydroxyethyl)ethylenediamine--.

Column 18, line 58, "slats" should read --salts--.

Signed and Sealed this

Eighth Day of November, 1994

Attest:

BRUCE LEHMAN

*Attesting Officer*     Commissioner of Patents and Trademarks